United States Patent
Sperling et al.

[11] Patent Number: 6,153,174
[45] Date of Patent: *Nov. 28, 2000

[54] COSMETIC COMPOSITIONS COMPRISING A COMBINATION OF UV ABSORBERS

[75] Inventors: Karin Sperling, Neustadt; Thomas Wünsch, Speyer; Horst Westenfelder, Neustadt; Beate Trentmann, Mannheim, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/948,254

[22] Filed: Oct. 9, 1997

[30] Foreign Application Priority Data

Oct. 22, 1996 [DE] Germany .............. 196 43 515

[51] Int. Cl.[7] ....................................... A61K 7/42
[52] U.S. Cl. .................... 424/59; 424/401; 424/78.03
[58] Field of Search ................. 424/59, 401, 78.03

[56] References Cited

U.S. PATENT DOCUMENTS 5,372,804 12/1994 Khoshdel et al. .................. 424/59
5,601,756 2/1997 Swearengin .................. 252/589
5,968,481 10/1999 Ascione et al. .

FOREIGN PATENT DOCUMENTS

| 087 098 | 2/1983 | European Pat. Off. . |
| 517 104 | 12/1992 | European Pat. Off. . |
| 570 838 | 11/1993 | European Pat. Off. . |
| 685 223 | 12/1995 | European Pat. Off. . |
| 796851 | 9/1997 | European Pat. Off. . |

*Primary Examiner*—Raj Bawa
*Attorney, Agent, or Firm*—Keil & Weinkauf

[57] ABSTRACT

The present invention relates to cosmetic compositions comprising a combination of sunscreen filters of the formula

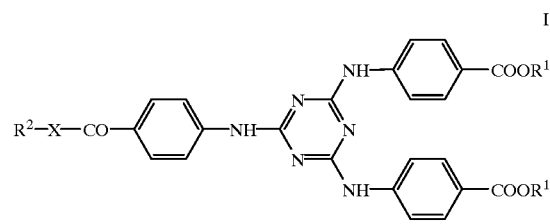

with other sunscreen filters.

5 Claims, No Drawings

COSMETIC COMPOSITIONS COMPRISING A COMBINATION OF UV ABSORBERS

The present invention relates to novel cosmetic compositions for topical use for protecting the skin and/or hair from UV radiation.

EP 087 098 discloses s-triazine derivatives of the formula (II) as UV-B filters, where R is, for example, open-chain alkyl radicals.

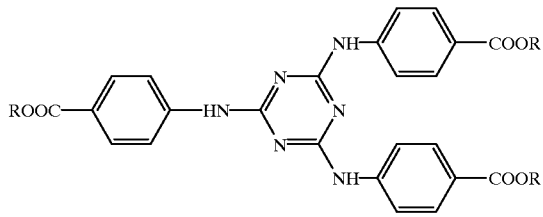

II

EP 517104 describes similar triazine derivatives of the formula (II), where R can be, for example, cycloalkyl radicals, and their use as UV filters in cosmetic preparations. These compounds are described as more advantageous than the compounds with open-chain radicals R.

EP 570 838 describes novel s-triazine derivatives of the formula (III) as light stabilizers for plastics and as cosmetic sunscreens.

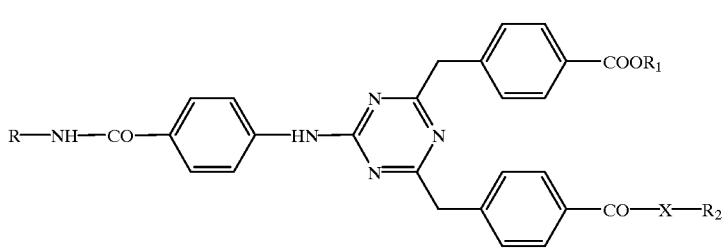

III

EP 685 223 describes cosmetic compositions which comprise a UV filter of the formula (II) with R=2-ethylhexyl (Uvinul® T150) and, in addition, as further ingredients, homomenthyl salicylate and/or octyl salicylate. The effect of these salicylates is faster solubilization of the Uvinul® T150 in certain solvents.

Although the compounds and compositions described above have good sunscreen properties, the requirements to be met by cosmetic sunscreens are continually increasing, so that the object was to provide cosmetic sunscreens which, in respect of one or more of the following properties, have even better values than the compositions hitherto disclosed:

The principal requirements of cosmetic sunscreens are:
1. UV-absorption range of maximum width,
2. high specific absorption in this range,
3. photo- and thermostability,
4. compatibility with skin (no irritant or toxic effects on the skin),
5. good skin feel and good adhesion to the skin,
6. resistance to water,
7. good compatibility with other cosmetic substances and good solubility,
8. in cosmetic solutions and preparations.

The invention relates to cosmetic compositions for topical use for protecting the skin and/or hair from UV radiation, comprising
(a) a UV filter A, B or C of the formula I, where

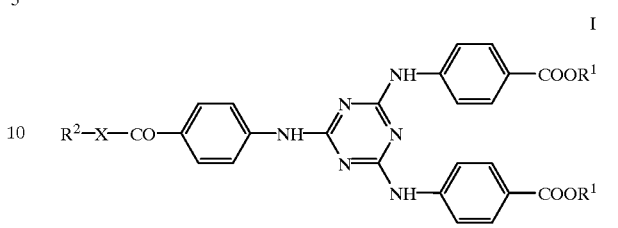

I

A for $R^1$=2-ethylhexyl, $R^2$=tert-butyl, X=NH;
B for $R^1$ and $R^2$=2-isopropyl-5-methyl-cyclohexyl, X=O;
C for $R^1$=methylcyclohexyl, $R^2$=2-ethylhexyl, X=O;

(b) another UV filter from the group of ethyl p-aminobenzoate (25 mol) ethoxylated, 2-ethylhexyl p-methoxycinnamate, 2-ethylhexyl 2-cyano-3,3-diphenylacrylate, 2-phenylbenzimidazolesulfonic acid and its salts, 2-hydroxy-4-methoxybenzophenone, 2-hydroxy-4-methoxybenzophenone-5-sulfonic acid, 3-(4'-methylbenzylidene)-d,l-camphor, 2,4,6-tri[p-(2-ethylhexoxycarbonyl)anilino]-1,3,5-triazine, 4-(tert-butyl)-4'-methoxydibenzoylmethane, as well as diluents, auxiliaries and carriers customary in cosmetics.

The cosmetic sunscreens according to the invention prove to be superior, in respect of one or more of the properties listed above, to sunscreens previously disclosed. The sunscreens show surprisingly good properties in particular with regard to the sun protection factor which can be achieved.

The UV filters (a) have the common formula (I), where the radicals have the following meaning:

Compound A: for $R^1$=2-ethylhexyl, $R^2$=tert-butyl, X=NH;
Compound B: for $R^1$ and $R^2$=2-isopropyl-5-methyl-cyclohexyl, X=O;
Compound C: for $R^1$=methylcyclohexyl, $R^2$=2-ethylhexyl; X=O The methyl group in $R^1$ in compound C can be in positions 2, 3 or 4 on the cyclohexyl radical.

Cosmetic products or preparations generally contain compounds (a) and (b) in amounts of from 0.1 to 15%, preferably 5–10%, of the weight of the formulation, besides the carriers or diluents customary in cosmetics, with or without conventional cosmetic auxiliaries.

The nature of the carrier, auxiliary or diluent determines whether the finished sunscreen-containing product is a solution, an oil, a cream, an ointment, a lotion, a gel or a powder. Preparations of these types can be found, for example, in the Journal "Seifen, Öle, Fette, Wachse", (1955) 147.

Examples of conventionally used cosmetic auxiliaries which are suitable as additives are emulsifiers, such as fatty alcohol ethoxylates, sorbitan fatty acid esters or lanolin derivatives, thickeners, such as carboxymethylcellulose or crosslinked polyacrylic acid, preservatives and perfumes.

Further auxiliaries are stabilizers such as magnesium or aluminum salts of fatty acids, complexing agents such as EDTA, antioxidants such as BHT, BHA or alpha-tocopherol.

Cosmetic oils used as auxiliaries are, for example, isopropyl esters of fatty acids, in particular isopropyl stearate, isopropyl palmitate, isopropyl isostearate, isopropyl myristate, isopropyl laurate, liquid paraffin and neutral oils.

Further ingredients of the cosmetic compositions according to the invention can be cosmetic agents such as panthenol, bisabolol, alpha-tocopherol, alpha-tocopherol acetate, aloe vera, seaweed extract and hyaluronic acid.

Examples of a base for sunscreen oils are vegetable oils such as arachis oil, olive oil, sesame oil, cotton seed oil, coconut oil, grape seed oil, castor oil or mineral oils, such as liquid petrolatum or, in particular, liquid paraffin, synthetic fatty acid esters and glycerides. Examples of a base for ointments are petrolatum, lanolin, eucerin or polyethylene glycols.

Examples of bases for creams are high-fat creams, glycerol, polysaccharide and Tylose creams, and, for creams based on fats and waxes, cetyl alcohol, lanolin cream, cocoa butter, beeswax, stearic acid, stearyl alcohol, glycerol monostearate, natural or mineral oils and fats.

Examples of bases for emulsions are mixtures of stearyl glycol, a vegetable and/or mineral oil, such as almond oil, liquid paraffin and petrolatum, and water or mixtures of ethyl alcohol, water, lanolin and tragacanth, or mixtures of ethyl alcohol, stearin, water, tragacanth and glycerol or mixtures of stearic acid, liquid paraffin, propyl or isopropyl alcohol and water.

The invention is illustrated further in the following examples.

All the numerical data in the following formulae are in grams.

EXAMPLE 1

Production of a cosmetic sunscreen in the form of a fat-free gel

| Product: | Fat-free sunscreen gel |
| --- | --- |
| 0.40 | Acrylates/C10–C30 alkyl acrylate cross |
| 0.25 | Hydroxyethylcellulose |
| 8.00 | Octyl methoxycinnamate |
| 1.00 | 4-Methylbenzylidenecamphor |
| 2.00 | UV Filter A |
| 0.20 | Disodium EDTA |
| q.s | Water |
| 5.00 | Glycerol |
| 0.15 | Fragrance |
| 0.30 | Imidazolidinylurea |
| 0.25 | Sodium methylparaben |
| 0.15 | Sodium propylparaben |
| 5.00 | PEG-25 PABA |
| 0.10 | Sodium hydroxide |

The gel has a sun protection factor (SPF, measured with an Optometrics SPF 290) of 13.

Comparative test:

A formulation in which the same amount of Uvinul T150 was used in place of UV filter A, but which was otherwise identical, has an SPF of 8.

EXAMPLE 2

Production of a cosmetic sunscreen in the form of a sun cream

| Product: | Sun cream |
| --- | --- |
| 6.00 | PEG-7-Hydrogenated castor oil |
| 5.00 | Zinc oxide |
| 5.00 | Isopropyl palmitate |
| 6.00 | Mineral oil |
| 3.00 | Octyl salicylate |
| 0.50 | Tocopheryl acetate |
| 8.00 | Octyl methoxycinnamate |
| 1.00 | 4-Methylbenzylidenecamphor |
| 2.00 | UV Filter A |
| 0.60 | Magnesium stearate |
| 2.00 | PEG-45/Dodecyl glycol copolymer |
| 0.25 | Methylparaben |
| 0.15 | Propylparaben |
| 5.00 | Imidazolidinylurea |
| 0.15 | Fragrance |
| 0.20 | Disodium EDTA |
| q.s | Water |

The cream has a sun protection factor (SPF, measured with an Optometrics SPF 290) of 16.

Comparative test:

A formulation in which the same amount of Uvinul T150 was used in place of UV filter A, but which was otherwise identical, has an SPF of 12.

EXAMPLE 3

Production of a cosmetic sunscreen in the form of a sunblock cream

| Product: | Sunblock cream |
| --- | --- |
| 5.00 | PEG-7-Hydrogenated castor oil |
| 4.00 | Isopropyl palmitate |
| 4.00 | Caprylic/capric triglyceride |
| 3.00 | UV Filter A |
| 1.50 | PEG-45/dodecyl glycol copolymer |
| 0.50 | Magnesium stearate |
| 1.50 | Dimethicone |
| 4.00 | Octyl methoxycinnamate |
| 4.00 | Octocrylene |
| 2.00 | 4-Methylbenzylidenecamphor |
| 2.00 | Titanium dioxide |
| 2.00 | Butylmethoxydibenzoylmethane |
| 4.00 | Glycerol |
| 8.00 | 611 Alcohol |
| q.s | Water |
| 5.00 | Propylene glycol |
| 0.15 | Fragrance |

The cream has a sun protection factor (SPF, measured with an Optometrics SPF 290) of 22.

Comparative test:

A formulation in which the same amount of Uvinul T150 was used in place of UV filter A, but which was otherwise identical, has an SPF of 16.

EXAMPLE 4

Production of a cosmetic sunscreen in the form of a sun milk

| Product: | SPF 6 Sun milk |
| --- | --- |
| 6.00 | PEG-7-Hydrogenated castor oil |
| 5.00 | Isopropyl palmitate |
| 10.00 | Mineral oil |
| 3.00 | Caprylic/capric triglyceride |
| 0.60 | Magnesium stearate |
| 3.00 | Octocrylene |
| 0.50 | Tocopheryl acetate |
| 2.00 | PEG-45/Dodecyl glycol copolymer |
| 0.05 | Tocopherol |
| 2.00 | UV Filter A |
| q.s | Water |
| 0.30 | Glycerol |
| 0.70 | Magnesium sulfate |
| 0.25 | Methylparaben |
| 0.15 | Propylparaben |
| 0.15 | Fragrance |

The gel has a sun protection factor (SPF, measured with an Optometrics SPF 290) of 8.
Comparative test:
A formulation in which the same amount of Uvinul T150 was used in place of UV filter A, but which was otherwise identical, has an SPF of 4.

EXAMPLE 5

Production of a cosmetic sunscreen in the form of a lip sunblock

| Product: | Lip sunblock |
| --- | --- |
| 48.00 | Eucerinum anhydricum |
| 2.00 | Bees wax |
| 2.00 | UV Filter A |
| 4.00 | Pentaerythrityl stearate/caprate/caprylate |
| 2.00 | Microcrystalline wax |
| 10.00 | Octyl methoxycinnamate |
| 3.00 | Glyceryl stearate SE |
| 10.00 | Glycerol |
| 2.00 | Quaternium-18 bentonite |
| 1.50 | PEG-45/Dodecyl glycol copolymer |
| 5.00 | Zinc oxide |
| 10.00 | Titanium dioxide |

The lip sunblock has a sun protection factor (SPF, measured with an Optometrics SPF 290) of 35.
Comparative test:
A formulation in which the same amount of Uvinul T150 was used in place of UV filter A, but which was otherwise identical, has an SPF of 28.

EXAMPLE 6

Production of a cosmetic sunscreen in the form of a sunblock milk

| Product: | Sunblock milk |
| --- | --- |
| 6.00 | PEG-7-Hydrogenated castor oil |
| 0.50 | Hydrogenated castor oil |
| 5.00 | Mineral oil |
| 10.00 | Octyl methoxycinnamate |
| 5.00 | Isoamyl p-methoxycinnamate |
| 2.00 | Butylmethoxydibenzoylmethane |
| 6.00 | Titanium dioxide |

-continued

| Product: | Sunblock milk |
| --- | --- |
| 2.00 | UV Filter A |
| 0.50 | Tocopheryl acetate |
| 2.00 | PEG-45/dodecyl glycol copolymer |
| 1.00 | Dimethicone |
| 3.00 | 4-Methylbenzylidenecamphor |
| q.s | Water |
| 0.50 | Phenoxyethanol |
| 5.00 | Propylene glycol |
| 0.20 | Disodium EDTA |

The sunblock milk has a sun protection factor (SPF, measured with an Optometrics SPF 290) of 30.
Comparative test:
A formulation in which the same amount of Uvinul T150 was used in place of UV filter A, but which was otherwise identical, has an SPF of 24.

We claim:

1. A cosmetic composition for topical use for protecting the skin or hair or both from UV radiation, consisting essentially of, in combination, synergistically effective amounts of (a) a UV filter selected from the group consisting of A and C having the formula I, where

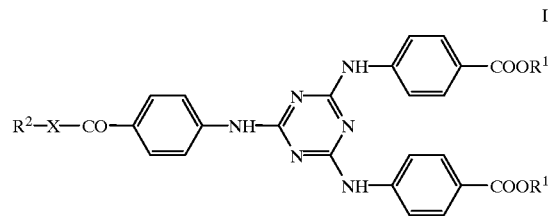

in A, $R^1$ is 2-ethylhexyl, $R^2$ is tert-butyl, X is NH;
in C, $R^1$ is methylcyclohexyl, $R^2$ is 2-ethylhexyl, X is O;

(b) another UV-filter selected from the group consisting of ethyl p-aminobenzoate (25 mol) ethoxylated, 2-ethylhexyl p-methoxycinnamate, 2-ethylhexyl 2-cyano-3,3-diphenylacrylate, 2-phenylbenzimidazolesulfonic acid and its salts, 2-hydroxy-4-methoxybenzophenone, 2-hydroxy-4-methoxybenzophenone-5-sulfonic acid, 3-(4'-methylbanzylidene)-d,1-camphor, 2,4,6-tri(p-(2-ethylhexoxycarbonyl)anilino)-1,3,5-triazine, 4-(tert-butyl)-4'-methoxydibenzoylmethane, as well as conventional cosmetic auxiliaries and carriers customary in cosmetics wherein said compounds (a) and (b) are in amounts ranging from 0.1 to 15% by weight of said composition.

2. A composition as claimed in claim 1, wherein compound A is the UV filter (a).

3. A composition as claimed in claim 1, wherein 2-ethylhexyl 2-cyano-3,3-diphenylacrylate is the UV filter (b).

4. A composition as claimed in claim 1, wherein 2-ethylhexyl p-methoxycinnamate is the UV filter (b).

5. A method for protecting skin or hair or both from UV radiation comprising applying to the skin or hair or both to be protected a combination, in synergistically effective amounts, consisting essentially of (a) a UV filter selected from the group consisting of A and C having the formula I, where

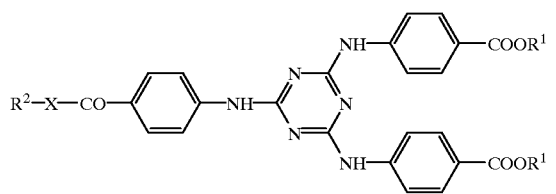

in A, $R^1$ is 2-ethylhexyl, $R^2$ is tert-butyl, X is NH;

in C, $R^1$ is methylcyclohexyl, $R^2$ is 2-ethylhexyl; X is O; and (b) another UV filter selected from the group consisting of ethyl p-aminobenzoate (25 mol) ethoxylated, 2-ethylhexyl p-methoxycinnamate, 2-ethylhexyl 2-cyano-3,3-diphenylacrylate, 2-phenylbenzimidazolesulfonic acid and its salts, 2-hydroxy-4-methoxybenzophenone, 2-hydroxy-4-methoxybenzophenone-5-sulfonic acid, 3-(4'-methylbenzylidene)-d,1-camphor, 2,4,6-tri(p-(2-ethylhexoxycarbonyl)anilino)]-1,3,5-triazine, 4-(tert-butyl)4'-methoxydibenzoylmethane, as sunscreen wherein said compounds (a) and (b) are in amounts ranging from 0.1 to 15% by weight of said composition.

* * * * *